Figure 2:
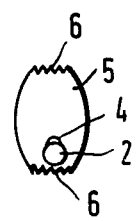

United States Patent [19]

Keller

[11] Patent Number: 4,657,549
[45] Date of Patent: Apr. 14, 1987

[54] ANCHORING ROD FOR TUBULAR BONES

[75] Inventor: Arnold Keller, Kayhude, Fed. Rep. of Germany

[73] Assignee: Waldemar Link GmbH & Co., Fed. Rep. of Germany

[21] Appl. No.: 763,751

[22] Filed: Aug. 7, 1985

Related U.S. Application Data

[63] Continuation of Ser. No. 630,037, Jul. 12, 1984, abandoned.

[30] Foreign Application Priority Data

Aug. 19, 1983 [DE] Fed. Rep. of Germany ....... 3330062

[51] Int. Cl.$^4$ .......................... A61F 2/28; A61F 5/04
[52] U.S. Cl. ..................... 623/16; 128/92 Y
[58] Field of Search ............... 128/92 R, 92 B, 92 A, 128/92 BA, 92 BB, 92 BC, 92 C, 92 CA, 92 D, 92 EA; 623/18, 19, 20, 21, 22, 23

[56] References Cited

U.S. PATENT DOCUMENTS

| 2,425,163 | 8/1947 | Reiwald | 4/413 |
| 2,489,870 | 11/1949 | Dzus | 128/92 B |
| 2,511,051 | 6/1950 | Dzus | 128/92 B |
| 2,765,787 | 10/1956 | Pellet | 128/92 CA |
| 3,046,565 | 7/1962 | Taylor | 4/414 |
| 4,269,180 | 5/1981 | Dall et al. | 128/92 B |
| 4,274,401 | 6/1981 | Miskew | 128/92 R |
| 4,275,717 | 6/1981 | Bolesky | 128/92 BC |
| 4,409,974 | 11/1983 | Freedland | 128/92 BC |
| 4,473,069 | 9/1984 | Kolmert | 128/92 B |

FOREIGN PATENT DOCUMENTS

| 765757 | 5/1953 | Fed. Rep. of Germany ... 128/92 BC |
| 195043 | 6/1967 | U.S.S.R. ........................ 728/92 BC |

Primary Examiner—Richard J. Apley
Assistant Examiner—David J. Isabella
Attorney, Agent, or Firm—Townsend and Townsend

[57] ABSTRACT

A device for anchoring a tension element in a tubular bone comprises an anchoring device attached eccentrically and in a hinged manner on the end of the tension element, the longitudinal dimension of the anchoring device being somewhat larger than the diameter of the medullary canal.

7 Claims, 4 Drawing Figures

ANCHORING ROD FOR TUBULAR BONES

This is a continuation Ser. No. 630,037 filed July, 12, 1984, now abandoned.

DESCRIPTION

The invention relates to a device for anchoring a tension element in a tubular bone.

In some cases, it is necessary or advantageous to set up compressive stresses in the longitudinal direction in a tubular bone, for example when treating fractures, or in combination with endoprostheses, in particular hip joint endoprostheses.

Devices of this type in which the tension element has to be fixed in the depth of the tubular bone by an anchoring device to be introduced at an angle into the bone from outside are known. However, the additional operation to introduce the anchoring device laterally from outside the bone is a problem. Moreover, devices in which the anchoring device is introduced into the medullary cavity from its end, and which comprise a multiplicity of mechanically expandable spikes which are intended to anchor themselves on the walls in the depth of the medullary cavity, are known. The disadvantage of devices of this type is the complicated mechanism necessary for expanding the spikes, which is susceptible to faults and whose loadbearing capacity is limited, since it is possible for the spikes to grip adequately only if they engage not only in the spongy substance but also in the cortical substance, but this is doubtful because of the hardness of the cortical substance and the dimensioning of the device which is predetermined by the bone.

The invention has the object of producing a device of the type mentioned in the introduction, which avoids these disadvantages.

According to the present invention, a tension element in the form of a rod is secured to an oblong anchoring device, preferably in the form of an oval plate, through a hinge-type connection along the longitudinal axis of the plate. The point of connection on the plate is eccentric with respect to the plate, causing the plate to tilt toward the tension rod during insertion of the latter into the medullary cavity of the bone, and then to tilt back toward the perpendicular when the rod is placed under tension, thereby anchoring the rod inside the bone.

On introduction of the tension rod, the anchoring device, due to its hinged connection to the tension rod, tilts more or less toward the latter, so that the cross-sectional dimensions of the device composed of the tension rod and the anchoring device are sufficiently smaller than the diameter of the medullary cavity into which it is to be pushed. When the tension rod is under tensile stress, due to force being exerted from one side, the plate tilts away from the tension rod and is locked against the walls of the medullary cavity. This locking can be promoted by indentations applied to the ends of the plate or, where appropriate, also on its sides.

The anchoring device remains stable in its anchoring position as long as its angle with the wall of the medullary cavity is greater than the angle of friction. Since the coefficient of friction of the sharp-edged anchoring device with respect to the rough cortical substance is very high, this condition allows a very great margin of latitude in the angle of the anchoring device. Moreover, this results in very wide limits for its longitudinal dimension. Thus, an exact adjustment to the diameter of the medullary cavity is unnecessary.

The eccentricity of the connection between the anchoring device and the tension rod needs to be only as large as is necessary to ensure the tilting of the anchoring device in the medullary cavity and thus the desired locking between the walls of the medullary cavity. Furthermore, it should not be considerably greater than is necessary for this purpose, so that the difference, resulting from this, in the stress on the two ends of the anchoring device is as small as possible. The claimed feature that the hinged connection between the anchoring device and the tension rod is provided at one end of the anchoring device should also be interpreted in this sense.

The swivelling axis of the hinge is at right-angles to the longitudinal axes of the tension rod and of the anchoring device. A very simple embodiment of the hinge comprises the tension rod being passed through a hole which is drilled in the anchor and whose diameter is considerably larger than that of the tension rod, the tension rod being thickened on both sides of the drilled hole, the thickening taking the form of, for example, a sphere, as can be produced by a welding bead.

Figure 1:
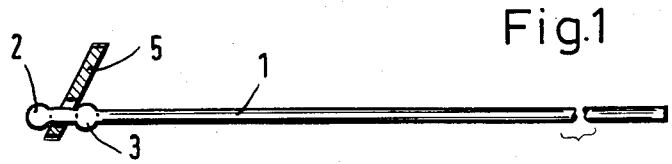

The invention is illustrated in detail below with reference to the drawing, which illustrates an advantageous exemplary embodiment. In this: FIG. 1 shows a side view of the device, FIG. 2 shows an end view of the device, FIG. 3 shows the principle of the anchoring when treating a fracture, and FIG. 4 shows the use of the device in association with a hip joint endoprosthesis.

The tension rod 1 has two spherical thickenings 2, 3 at one end. Between these, it passes through the hole 4 drilled in the anchoring device 5 which is in the form of a plate, the diameter of the drilled hole being smaller than the diameter of the spherical thickenings 2 and 3. The anchoring device 5 has an oval outline, its shorter transverse axis being smaller than the diameter of the medullary canal, while its longer axis is larger, preferably by a factor of 1.05–1.4, than the diameter of the medullary cavity. The ends have indentations 6 to improve the anchoring to the inner surface of the cortical substance of the bone.

The diameter of the drilled hole 4 is larger than the diameter of the rod 2 to an extent sufficient for the anchoring device on the rod to tilt into a position in which each dimension measured at right-angles to the longitudinal axis of the rod is smaller than the diameter of the medullary cavity.

Figure 3:
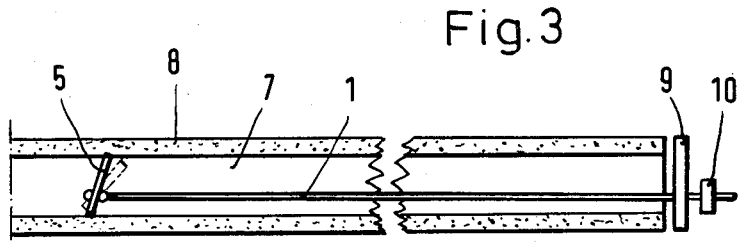
Figure 4:
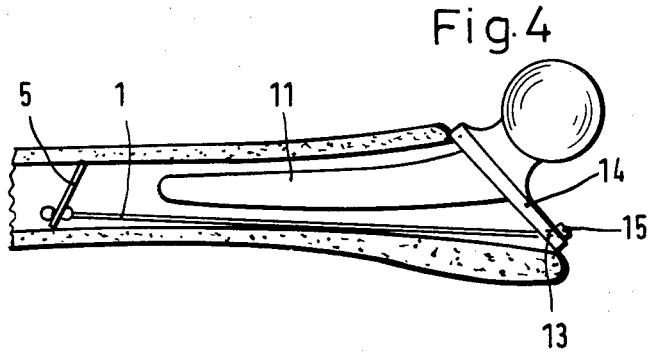

This latter feature permits the device to be pushed in the longitudinal direction into the medullary cavity 7 of a bone 8, in accordance with FIG. 3, during which the anchoring device is swivelled with respect to the tension rod into the position shown by the dotted line. When a tensile force is subsequently exerted on the tension rod, then the anchoring device tilts into the position illustrated by the full lines, in which position it locks fast onto the inner walls of the cortical substance 8 and thus forms a reliable end support when the parts of the bone, which are shown separated, are tensioned together in the longitudinal direction by means of the tension rod, the other end of which is provided with an end support plate 9 and a nut 10.

FIG. 4 shows an analogous application in association with a hip joint femoral prosthesis 11. The tension rod 1, which is anchored in the femur 12 by means of the anchoring device 5, is passed proximally through a drilled hole 13 in the neck support plate 14 of the prosthesis 11 and is tensioned by means of a nut 15. Thus, the involvement of the medial part of the bone 12 and the transmission of force to the prosthesis can be increased.

I claim:

1. Apparatus for anchoring a tubular bone having a medullary cavity of a given diameter, said apparatus comprising:
   a tension rod;
   an ablong plate having a longitudinal axis greater than said given diameter, a transverse axis less than said given diameter, and an eccentric hole sized for loose passage of said tension rod therethrough; and
   first and second heads along said tension rod capable of retaining said oblong plate therebetween.

2. Apparatus according to claim 1 in which said oblong plate has one edge of curved shape.

3. Apparatus according to claim 1 in which said oblong plate is oval in shape.

4. Apparatus according to claim 1, 19 or 20 further comprising serrations along the edges of said oblong plate at each end of said longitudinal axis capable of anchoring said plate to the inner surface of said medullary cavity.

5. Apparatus according to claim 1 in which said longitudinal axis is about 1.05 to about 1.4 times said given diameter.

6. Apparatus according to claim 1 further comprising means for applying elongating tension to said tension rod to tilt said oblong plate with respect thereto and thereby anchor the edges of said oblong plate at each end of said longitudinal axis against the inner surface of said medullary cavity.

7. Apparatus for anchoring a tubular bone having a medullar cavity of a given diameter, said apparatus comprising:
   a tension rod;
   a plate of oval shape, having a longitudinal axis greater than said given diameter, a transverse axis less than said given diameter, and serrations along the rim thereof at each end of said longitudinal axis, said plate being tiltably mounted to said tension rod at one end thereof at a point on said plate off-center along said longitudinal axis; and
   means at the other end of said tension rod for applying sufficient elongating tension to said tension rod to tilt said plate when resistance is applied to said serrations.

* * * * *